United States Patent
Sakai et al.

(10) Patent No.: US 7,892,526 B2
(45) Date of Patent: Feb. 22, 2011

(54) HAIR COSMETIC COMPOSITION

(75) Inventors: Hirokazu Sakai, Tokyo (JP); Hiroto Tanamachi, Tokyo (JP); Yoshimasa Okamoto, Tokyo (JP); Koji Morita, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/406,170

(22) Filed: Mar. 18, 2009

(65) Prior Publication Data

US 2009/0181059 A1 Jul. 16, 2009

Related U.S. Application Data

(62) Division of application No. 10/743,834, filed on Dec. 24, 2003, now abandoned.

(30) Foreign Application Priority Data

Dec. 25, 2002 (JP) ............... 2002-375321
Dec. 25, 2002 (JP) ............... 2002-375322

(51) Int. Cl.
*A61Q 5/00* (2006.01)
*A61Q 5/02* (2006.01)
*A61Q 5/12* (2006.01)

(52) U.S. Cl. ............... 424/70.12; 424/70.21; 424/70.31

(58) Field of Classification Search ............... None
See application file for complete search history.

(56) References Cited

U.S. PATENT DOCUMENTS

| | | | |
|---|---|---|---|
| 5,034,218 A | 7/1991 | Duvel | |
| 5,656,668 A | 8/1997 | Motion et al. | |
| 5,679,357 A | 10/1997 | Dubief et al. | |
| 5,977,038 A | 11/1999 | Birtwistle et al. | |
| 6,060,612 A | 5/2000 | Hong et al. | |
| 6,468,515 B1 * | 10/2002 | Uchiyama et al. | 424/70.27 |
| 6,685,953 B1 | 2/2004 | Hoshino et al. | |
| 6,719,967 B1 * | 4/2004 | Brown et al. | 424/70.1 |
| 6,923,954 B2 * | 8/2005 | Doi et al. | 424/70.19 |
| 2003/0208858 A1 | 11/2003 | Hirano | |
| 2003/0215410 A1 | 11/2003 | Hirano | |
| 2003/0215416 A1 | 11/2003 | Hirano | |
| 2004/0115162 A1 | 6/2004 | Hoshino et al. | |
| 2005/0095212 A1 | 5/2005 | Hirano | |
| 2005/0095217 A1 | 5/2005 | Hirano | |

FOREIGN PATENT DOCUMENTS

| | | | |
|---|---|---|---|
| EP | 1 166 766 A1 | | 1/2002 |
| EP | 1283030 | * | 2/2003 |
| JP | 48-18810 | | 6/1973 |
| JP | 6-502660 | | 3/1994 |
| JP | 8-502058 | | 3/1996 |
| JP | 9-165317 | | 6/1997 |
| JP | 10-226674 | | 8/1998 |
| JP | 2002-500173 | | 1/2002 |
| JP | 2002-53444 | | 2/2002 |
| JP | 2002-53445 | | 2/2002 |
| WO | 93/02656 | | 2/1993 |
| WO | 99/34768 | | 7/1999 |
| WO | 00/61097 | | 10/2000 |
| WO | WO 00/61097 | * | 10/2000 |

OTHER PUBLICATIONS

K. De Polo, "A Short Textbook of Cosmetology", Verlag für Die Chemische Industrie, XP-002295631, pp. 64-69 (1998).
"Koushouhin seizougaku, technique and practical", Published by Frangrance Journal, Ver. 1, first copy, pp. 299-321 (with partial English translation)(Aug. 25, 2001).

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

Provided is a hair cosmetic composition containing (A) an amphipathic amide lipid, (B) a cationic surfactant or a tertiary amine type compound represented by the following formula (N):

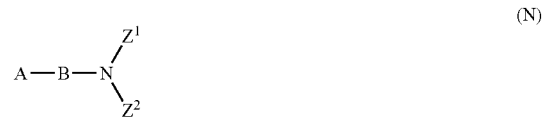

wherein, A represents a hydrogen atom or a linear or branched, saturated or unsaturated amide, (N-hydrocarbon) carbamoyl, acyloxy or hydrocarbonoxy group each having 12 to 24 carbon atoms in total, B represents a linear or branched, saturated or unsaturated $C_{1-22}$ hydrocarbon group, and $Z^1$ and $Z^2$ each represents a $C_{1-4}$ alkyl group; or a salt of the compound, and (C) a silicone; and having a pH at 25° C. of from 1 to 4.5 when diluted with water to 20 times the weight of the composition.

7 Claims, No Drawings

HAIR COSMETIC COMPOSITION

This is a divisional application of U.S. application Ser. No. 10/743,834, filed Dec. 24, 2003.

FIELD OF THE INVENTION

The present invention relates to hair cosmetic compositions containing an amphipathic amide lipid, and a silicone.

BACKGROUND OF THE INVENTION

Since hair is daily exposed to physical stimulation by daily hair care routines such as heat drying with a hair dryer and brushing, and chemical stimulation by shampooing, permanent weaving, dyeing and bleaching, it is in a damaged state with a partial loss of components or structure. A change in hair quality due to ageing accelerates this damage and also causes the loss of suppleness which healthy hair inherently possesses.

It is a common practice to protect or repair hair in a damaged state by making up for the lost components or structure or analogue thereof. Interaction (affinity) between a protecting base and hair is considered to be important for developing a protecting or restoring function, and thus a method of using a sphingolipid or protein derivative as a protecting base has been used widely as a useful technique. For example, proposed is a cationic dispersing agent for hair care or hair protection containing a ceramide or glycoceramide and a specific quaternary ammonium compound (Japanese Patent Application Laid-Open No. 502660/1994). The agent however cannot contain a sufficient amount of a protecting base such as a ceramide or glycoceramide because it has a high melting point and is liable to crystallize. Moreover, this protecting base, through added in a slight amount, does not readily penetrate into hair. The conventional hair cosmetic composition is therefore accompanied by the problem that the protecting base incorporated therein cannot fully function, because it cannot be fed to hair in an adequate amount.

In addition, it is difficult to incorporate the above-described protecting base stably in the hair cosmetic composition because it has a high melting point. There is also a problem that the protecting base is liable to cause separation, gelation or crystallization with the passage of time.

SUMMARY OF THE INVENTION

According to the present invention, there is thus provided a hair cosmetic composition containing the following components (A) to (C):

(A): an amphipathic amide lipid, (B): a cationic surfactant, or a tertiary amine type compound represented by the following formula (N):

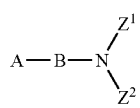

(N)

wherein, A represents a hydrogen atom, or a linear or branched, saturated or unsaturated amide, (N-hydrocarbon) carbamoyl, acyloxy or hydrocarbonoxy group, each having 12 to 24 carbon atoms in total, B represents a linear or branched, saturated or unsaturated divalent $C_{1-22}$ hydrocarbon group, and $Z^1$ and $Z^2$ each independently represents a $C_{1-4}$ alkyl group; or a salt of the compound, and (C): a silicone. The composition has a pH at 25° C. of from 1 to 4.5 when diluted with water to 20 times the weight, by weight of the composition.

DETAILED DESCRIPTION OF THE INVENTION

The present invention relates to a hair cosmetic composition which has benefits including ability to allow a protecting base incorporated therein to penetrate into hair sufficiently, has excellent effects of preventing or repairing hair damage, and has excellent storage stability.

The present inventors have found that, by incorporating a cationic surfactant or a specific tertiary amine type compound or a salt thereof and a silicone into an amphipathic amide lipid serving as a protecting base and by acidifying the system, the amphipathic amide lipid can readily penetrate into hair and the hair is protected from physical or chemical stimulation, whereby split ends or broken hair is prevented; hair is significantly imparted with a pleasant touch such as natural smoothness, moist feeling and suppleness which healthy hair inherently possesses; and the storage stability of the composition is greatly improved.

The amphipathic amide lipid as Component (A) preferably has 1 or 2 amide groups; preferably has, as a carbon chain bonded to the carbonyl group of the amide group, a $C_{5-60}$ alkyl or alkylene group which may be substituted with a hydroxy group and may contain an ester bond in its main chain; and preferably contains 1 to 5 hydroxy or $C_{1-30}$ alkoxy groups in total. The following compounds (1) to (4) are specific preferred examples of the amphipathic amide lipid.

(1) Diamide compounds represented by formula (1):

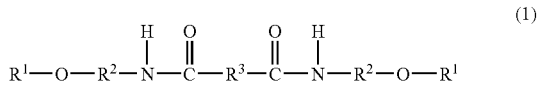

(1)

wherein, $R^1$ represents a linear or branched $C_{1-12}$ hydrocarbon group which may be substituted with a hydroxy group(s) and/or alkoxy group(s), $R^2$ represents a linear or branched divalent $C_{1-5}$ hydrocarbon group and $R^3$ represents a linear or branched divalent $C_{1-22}$ hydrocarbon group.

As $R^1$ in formula (1), linear or branched $C_{1-12}$ alkyl groups which may be substituted with 1 to 3 groups selected from the group consisting of a hydroxy group and $C_{1-6}$ alkoxy groups are preferred. Of these, unsubstituted $C_{1-12}$ alkyl groups and $C_{2-12}$ alkyl groups substituted with 1 to 2 hydroxy groups and one $C_{1-6}$ alkoxy group or with one hydroxy group and one $C_{1-6}$ alkoxy group are more preferred. Specific examples include methyl, ethyl, propyl, butyl, hexyl, dodecyl, 2-methylpropyl, 2-ethylhexyl, 2-hydroxyethyl, 9-hydroxynonyl, 2,3-dihydroxypropyl, 2-methoxyethyl, 2-hydroxy-3-methoxypropyl and 9-methoxynonyl groups, of which 2-hydroxyethyl, methyl, dodecyl and 2-methoxyethyl groups are preferred.

As $R^2$ in formula (1), linear or branched $C_{2-5}$ alkylene groups are preferred, and linear or branched $C_{2-3}$ alkylene groups are preferred. Specific examples include ethylene, trimethylene, tetramethylene, pentamethylene, 1-methylethylene, 2-methylethylene, 1-methyltrimethylene, 2-methyltrimethylene, 1,1-dimethylethylene and 2-ethyltrimethylene groups. Of these, ethylene and trimethylene groups are preferred.

As $R^3$ in formula (1), linear or branched divalent $C_{2-22}$ hydrocarbon groups are preferred, and linear or branched $C_{11-22}$ alkylene groups and alkenylene groups having 1 to 4 double bonds are more preferred. Specific examples include ethylene, trimethylene, tetramethylene, hexamethylene, heptamethylene, octamethylene, decamethylene, undecamethylene, dodecamethylene, tridecamethylene, tetradecamethylene, hexadecamethylene, octadecamethylene, 1-methylethylene, 2-ethyltrimethylene, 1-methylheptamethylene, 2-methylheptamethylene, 1-butylhexamethylene, 2-methyl-5-ethylheptamethylene, 2,3,6-trimethylheptamethylene, 6-ethyldecamethylene, 7-methyltetradecamethylene, 7-ethylhexadecamethylene, 7,12-dimethyloctadecamethylene, 8,11-dimethyloctadecamethylene, 7,10-dimethyl-7-ethylhexadecamethylene, 1-octadecylethylene, ethenylene, 1-octadecenylethylene, 7,11-octadecadienylene, 7-ethenyl-9-hexadecamethylene, 7,12-dimethyl-7,11-octadecadienylene and 8,11-dimethyl-7,11-octadecadienylene groups. Of these, 7,12-dimethyloctadecamethylene, 7,12-dimethyl-7,11-octadecadienylene, octadecamethylene, undecamethylene and tridecamethylene groups are preferred.

Preferred diamide compounds (1) are compounds having the above-described preferred groups as $R^1$, $R^2$ and $R^3$, respectively. Specific examples are the following compounds:

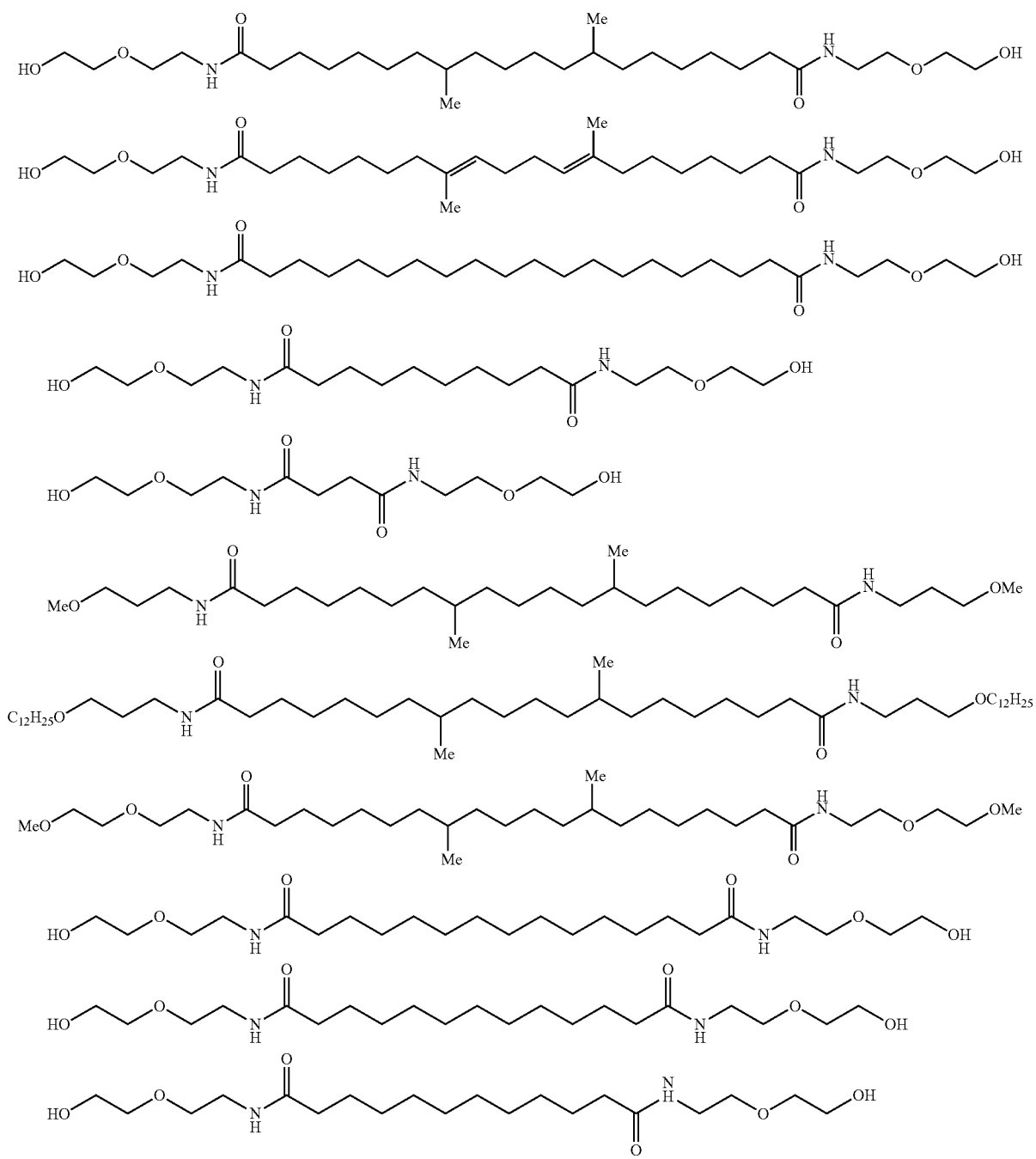

-continued

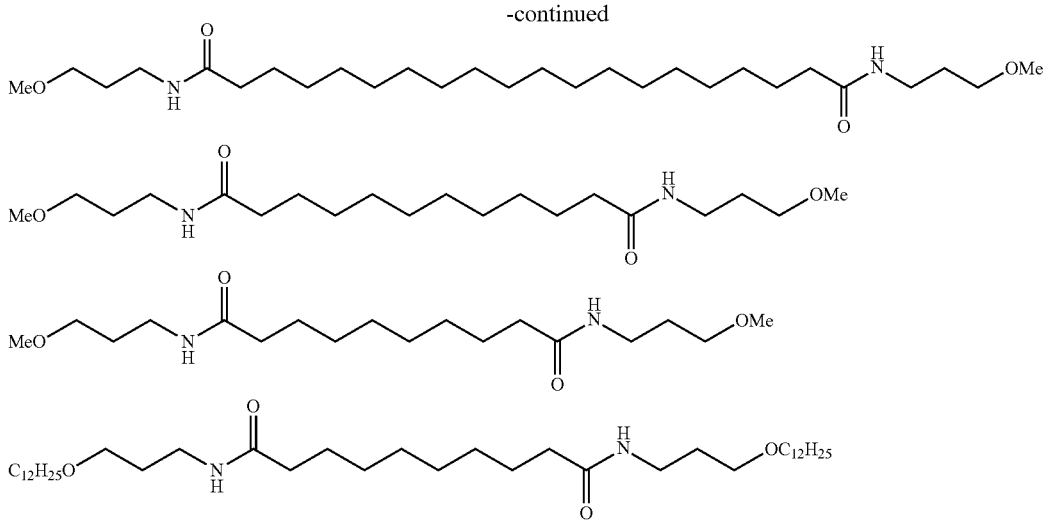

(2) Ceramides represented by the following formula (2):

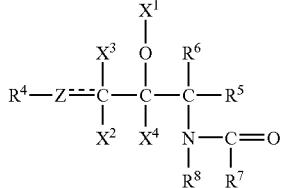

wherein, $R^4$ represents a linear, branched or cyclic, saturated or unsaturated $C_{4-30}$ hydrocarbon group which may be substituted with hydroxy, oxo or amino group(s), Z represents a methylene group, a methine group or an oxygen atom, a broken line represents the presence or absence of a π bond, $X^1$ represents a hydrogen atom, an acetyl group or a glyceryl group, or, together with the adjacent oxygen atom, forms an oxo group, $X^2$, $X^3$ and $X^4$ each independently represents a hydrogen atom, a hydroxy group or an acetoxy group (with the proviso that when Z represents a methine group, one of $X^2$ and $X^3$ represents a hydrogen atom and the other does not exist, and when —O—$X^1$ represents an oxo group, $X^4$ does not exist), $R^5$ and $R^6$ each independently represents a hydrogen atom, a hydroxy group or a hydroxymethyl group, $R^7$ represents a linear, branched or cyclic, saturated $C_{5-35}$ hydrocarbon group which may be substituted with a hydroxy or amino group, or the saturated $C_{5-35}$ hydrocarbon group in which a linear, branched or cyclic, saturated or unsaturated $C_{8-22}$ fatty acid which may be substituted with a hydroxy group(s) is ester-bonded at the ω-position of the hydrocarbon group, and $R^8$ represents a hydrogen atom or a linear or branched, saturated or unsaturated hydrocarbon group which may have substituent(s) selected from a hydroxy group, hydroxyalkoxy groups, alkoxy groups and an acetoxy group, and has 1 to 8 carbon atoms in total.

As $R^4$ in formula (2), linear, branched or cyclic, saturated or unsaturated $C_{7-22}$ hydrocarbon groups which may be substituted with hydroxy group(s) are preferred. As $X^1$, a hydrogen atom and a glyceryl group are preferred. It is preferred that none or one of $X^2$, $X^3$, and $X^4$ represents a hydroxy group and the others represent a hydrogen atom. It is preferred that one of $R^5$ and $R^6$ represents a hydrogen atom or a hydroxymethyl group and the other represents a hydrogen atom. In $R^7$, preferred examples of the fatty acid which may be ester-bonded or amide-bonded to the saturated hydrocarbon group at the ω-position thereof include isostearic acid, 12-hydroxystearic acid and linoleic acid. As $R^8$, a hydrogen atom and hydrocarbon groups which may be substituted with 1 to 3 substituents selected from the group consisting of a hydroxy group, hydroxyalkoxy groups and alkoxy groups and have 1 to 8 carbon atoms in total are preferred.

As ceramide (2), preferred are the following compounds (2a) and (2b).

(2a) Natural ceramides or natural type ceramides represented by formula (2a), and derivatives thereof (which will hereinafter be called "natural type ceramides")

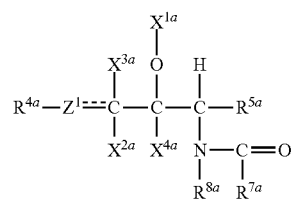

wherein, $R^{4a}$ represents a linear, branched or cyclic, saturated or unsaturated $C_{7-19}$ hydrocarbon group which may be substituted with a hydroxy group, $Z^1$ represents a methylene or methine group, a broken line represents the presence or absence of a π bond, $X^{1a}$ represents a hydrogen atom or, together with the adjacent oxygen atom, forms an oxo group, $X^{2a}$, $X^{3a}$ and $X^{4a}$ each independently represents a hydrogen atom, a hydroxy group or an acetoxy group (with the proviso that when $Z^1$ represents a methine group, one of $X^{2a}$ and $X^{3a}$ represents a hydrogen atom and the other does not exist, and when —O—$X^{1a}$ represents an oxo group, $X^{4a}$ does not exist), $R^{5a}$ represents a hydroxymethyl group, $R^{7a}$ represents a linear, branched or cyclic, saturated $C_{5-30}$ hydrocarbon group which may be substituted with hydroxy group(s), or the saturated $C_{5-30}$ hydrocarbon group in which a linear or branched, saturated or unsaturated $C_{8-22}$ fatty acid which may be substituted with hydroxy group(s) is ester-bonded at the ω-position of the hydrocarbon group, and $R^{8a}$ represents a hydrogen atom or a $C_{1-4}$ alkyl group.

Preferred are compounds in which $R^{4a}$ is a linear $C_{7-19}$, more preferably $C_{13-15}$ alkyl group, $Z^1$ is a methine group, one of $X^{2a}$ and $X^{3a}$ is a hydrogen atom, and $R^{7a}$ is a linear $C_{9-27}$ alkyl group which may be substituted with hydroxy group(s). In addition, $X^{1a}$ preferably represents a hydrogen atom or, together with an oxygen atom, forms an oxo group. More preferred examples of $R^{7a}$ include a tricosyl group, a 1-hydroxypentadecyl group, a 1-hydroxytricosyl group, a hepta-decyl group, a 1-hydroxyundecyl group and a nonacosyl group having a linoleic acid ester-bonded at the ω-position of the group.

Specific examples of the natural type ceramides include Ceramide Types 1 to 7 having the below-described structures and obtained by amidation of sphingosine, dihydrosphingosine, phytosphingosine or sphingadienine (for example, FIG. 2 of J. Lipid Res., 24, 759 (1983), and pig and human ceramides as described in FIG. 4 of J. Lipid Res., 35, 2069 (1994)).

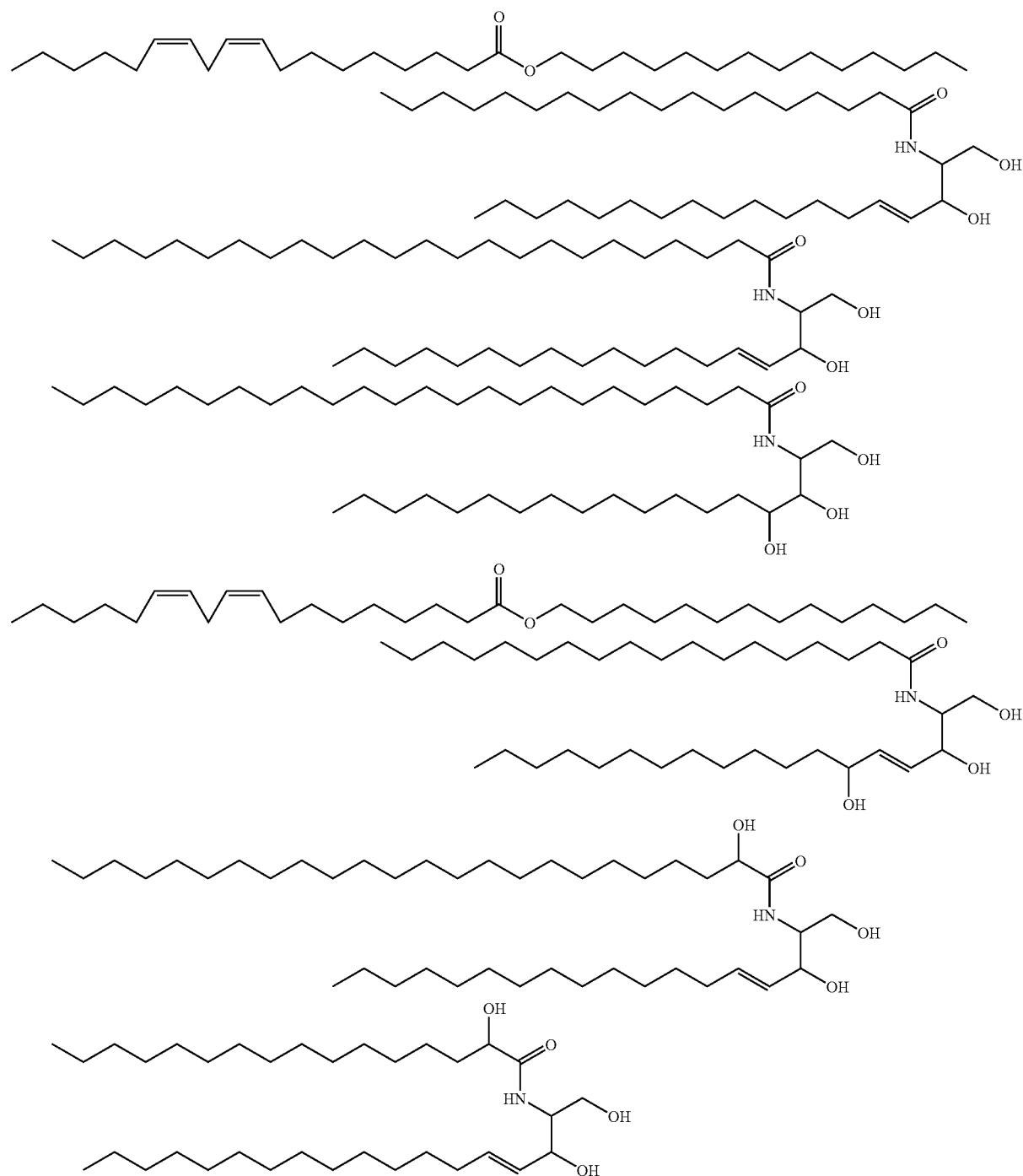

-continued

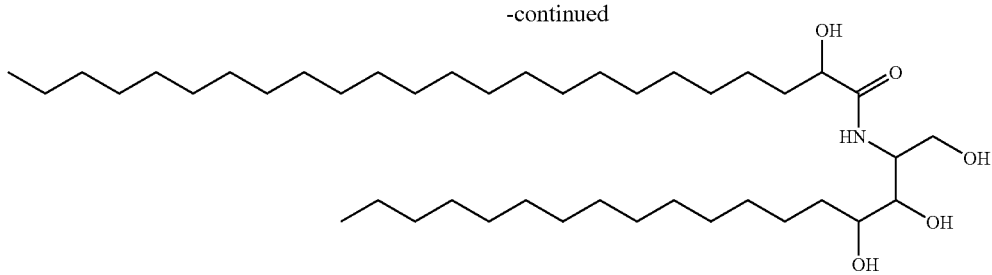

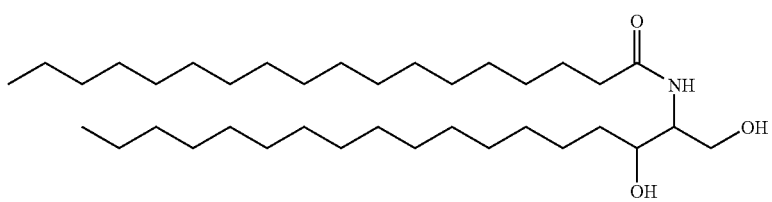

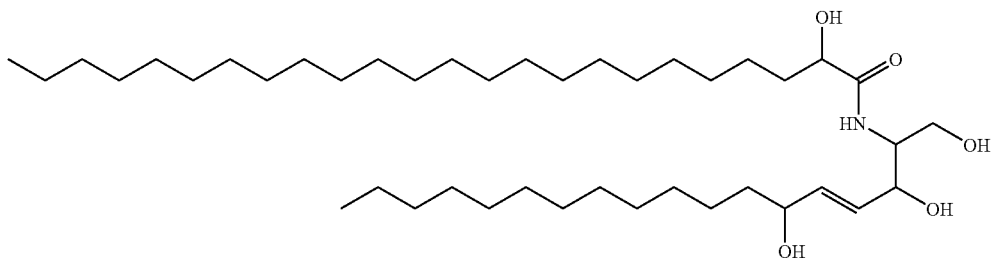

Examples also include N-alkyl derivatives (for example, N-methyl derivatives) of the above-described ceramides. They may be either a natural extract or synthesized product. Commercially available ones are also usable.

(2b) Pseudo type ceramides represented by the following formula (2b):

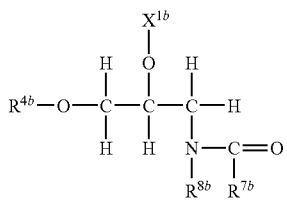

wherein, $R^{4b}$ represents a linear, branched or cyclic, saturated or unsaturated $C_{10-22}$ hydrocarbon group which may be substituted with hydroxy group(s), $X^{1b}$ represents a hydrogen atom, an acetyl group or a glyceryl group, $R^{7b}$ represents a linear, branched or cyclic, saturated or unsaturated $C_{5-22}$ hydrocarbon group which may be substituted with hydroxy or amino group(s), or the hydrocarbon group in which a linear or branched, saturated or unsaturated $C_{8-22}$ fatty acid which may be substituted with hydroxy group(s) is ester-bonded at the ω-position of the hydrocarbon group, and $R^{8b}$ represents a hydrogen atom or an alkyl group which may be substituted with hydroxy group(s), hydroxyalkoxy group(s), alkoxy group(s) or acetoxy group(s) and has 1 to 8 carbon atoms in total.

Preferred as $R^{7b}$ are a nonyl group, a tridecyl group, a pentadecyl group, an undecyl group having linoleic acid ester-bonded at the ω-position of the group, a pentadecyl group having linoleic acid ester-bonded at the ω-position of the group, a pentadecyl group having 12-hydroxystearic acid ester-bonded at the ω-position of the group, and an undecyl group having methyl-branched isostearic acid amide-bonded at the ω-position of the group. As the hydroxyalkoxy or alkoxy groups for $R^{8b}$, preferred are those having 1 to 8 carbon atoms.

As the pseudo type ceramides (2b), those having as $R^{4b}$ a hexadecyl group, as $X^{1b}$ a hydrogen atom, as $R^{7b}$ a pentadecyl group, and as $R^{8b}$ a hydroxyethyl group; those having as $R^{4b}$ a hexadecyl group, as $X^{1b}$ a hydrogen atom, as $R^{7b}$ a nonyl group, and as $R^{8b}$ a hydroxyethyl group; or those having as $R^{4b}$ a hexadecyl group, as $X^{1b}$ a glyceryl group, as $R^{7b}$ a tridecyl group, and as $R^{8b}$ a 3-methoxypropyl group are preferred, with those having as $R^{4b}$ a hexadecyl group, as $X^{1b}$ a hydrogen atom, as $R^{7b}$ a pentadecyl group, and as $R^{8b}$ a hydroxyethyl group being more preferred. Specific preferred examples include those represented by the following formulas:

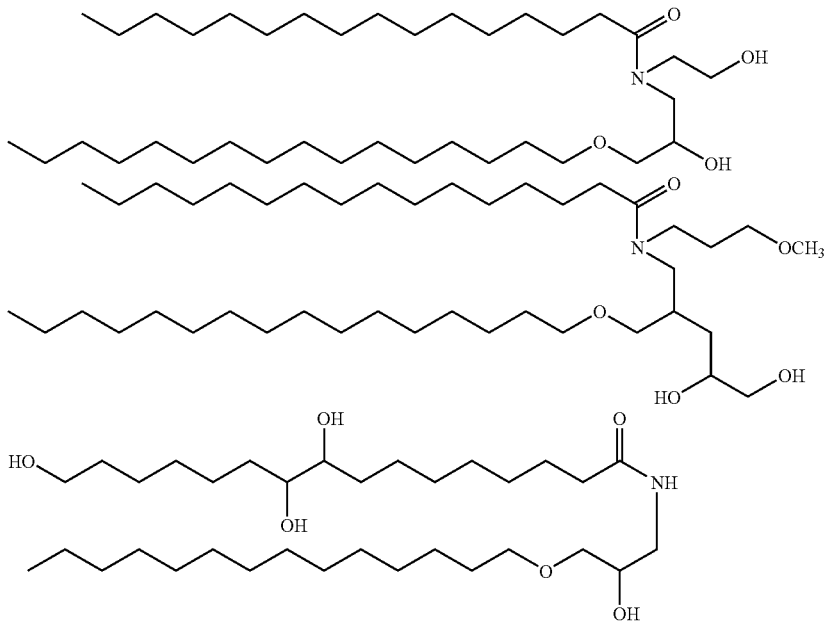

(3) Diamide compounds represented by the following formula (3):

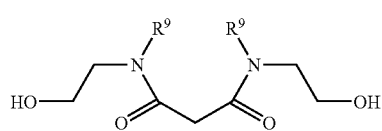

wherein, $R^9$ represents a $C_{10-18}$ alkyl group which may be substituted with hydroxy group(s).

Specific examples of compound (3) include the compound represented by the following formula:

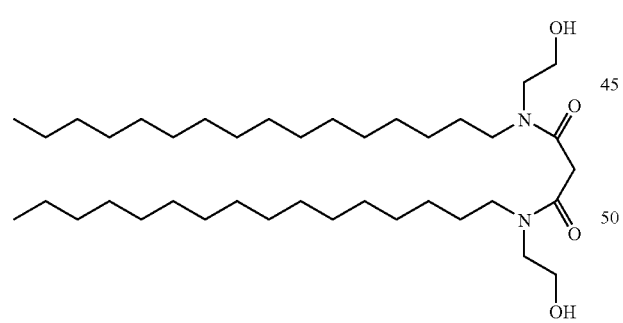

(4) Amide compounds represented by the following formula (4):

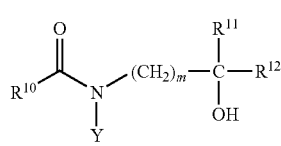

wherein, $R^{10}$ represents a linear or branched, saturated or unsaturated $C_{9-31}$ alkyl group which may be substituted with hydroxy group(s), or a 2-dodecen-1-yl succinic acid residue, m stands for an integer of from 1 to 3, $R^{11}$ and $R^{12}$ each represents a hydrogen atom or a $C_{1-4}$ alkyl or hydroxyalkyl group, Y represents a linear or branched, saturated or unsaturated $C_{10-32}$ alkyl group which may be substituted with hydroxy group(s), or a substituent represented by the following formula:

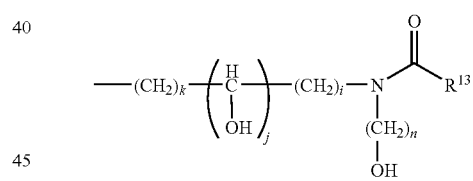

in which, k, i and n each stands for an integer of from 1 to 3, j stands for 0 or 1, and $R^{13}$ represents a linear or branched, saturated or unsaturated $C_{9-31}$ alkyl group which may be substituted with hydroxy group(s).

Specific examples of Compound (4) include a compound represented by the following formula:

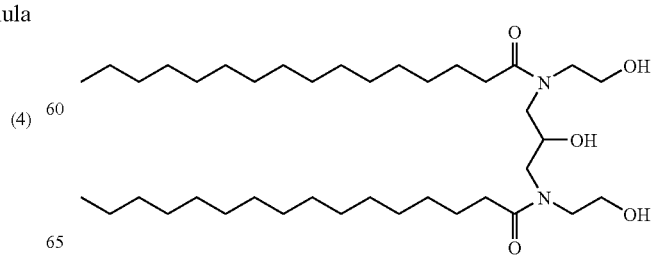

Of the above-described amphipathic amide lipids, those represented by formula (1) or (2) are preferred, and those represented by formula (1) are more preferred.

As Component (A), two or more of these amphipathic amide lipids may be used in combination. Its (their) content in the hair cosmetic composition of the present invention is preferably from 0.001 to 20 wt. %, more preferably from 0.15 to 15 wt. %, even more preferably from 0.2 to 3 wt. %, by weight of the composition, in view of imparting suppleness to hair and preventing split ends or breakage of hair.

Examples of cationic surfactant (B) include lauryl trimethylammonium chloride, cetyl trimethylammonium chloride, cetyl trimethylammonium bromide, stearyl trimethylammonium chloride, stearyl trimethylammonium bromide, lauryl trimethylammonium bromide, dialkyl dimethylammonium chlorides, dicetyl dimethylammonium chloride, distearyl dimethylammonium chloride, dicocoyl dimethylammonium chloride, myristyl dimethylbenzylammonium chloride, stearyl dimethylbenzylammonium chloride, lanolin fatty acid aminopropylethyldimethylammonium ethylsulfate, lanolin fatty acid aminoethyltriethylammonium ethylsulfate, lanolin fatty acid aminoethyldiethylmethylmmonium ethylsulfate, lanolin fatty acid aminoethyltrimethylammonium ethylsulfate, lanolin fatty acid aminopropyltriethylammonium ethylsulfate, lanolin fatty acid aminoethyltrimethylammonium methylsulfate, lanolin fatty acid aminopropylethyldimethylammonium methylsulfate, isoalkanoic acid (C14 to C20) aminopropylethyldimethylammonium ethylsulfates, isoalkanoic acid (C18 to C22) aminopropylethyldimethylammonium ethylsulfates, isostearic acid aminopropylethyldimethylammonium ethylsulfate, isononanoic acid aminopropylethyldimethylammonium ethylsulfate and alkyltrimethylammonium saccharines.

In the formula (N) representing the tertiary amine type compound as Component (B), when A represents a group other than a hydrogen atom, A is preferably an acyloxy or hydrocarbon oxy group having 14 to 22, preferably 18 to 22 carbon atoms in total. Moreover, the hydrocarbon moiety of the compound is preferably saturated, more preferably linear and saturated. In this case, a trimethylene group is even more preferred as B. When A is a hydrogen atom, on the other hand, B preferably represents a $C_{18-22}$ group, of which saturated groups are preferred, and saturated and linear groups are more preferred. Examples of $Z^1$ and $Z^2$ include methyl, ethyl, propyl, isopropyl, butyl and tert-butyl groups, with methyl and ethyl groups being preferred and methyl group being more preferred. Specific examples include N,N-dimethyloctadecyloxypropylamine and stearamidopropyldimethylamine.

The salt of the tertiary amine type compound as Component (B) is formed by neutralizing reaction between the tertiary amine type compound and an acidic amino acid, organic acid or inorganic acid. Acidic amino acids include glutamic acid and aspartic acid, with glutamic acid being preferred. Organic acids include carboxylic acids such as monocarboxylic acids, dicarboxylic acids, hydroxycarboxylic acids and polycarboxylic acids, alkylsulfuric acids and alkylphosphoric acids. Of these, carboxylic acids are preferred and dicarboxylic acids and hydroxycarboxylic acids are more preferred. Dicarboxylic acids include malonic acid, succinic acid, glutaric acid, adipic acid, maleic acid, fumaric acid and phthalic acid, while hydroxycarboxylic acids include glycolic acid, lactic acid, hydroxyacrylic acid, oxybutyric acid, glyceric acid, malic acid, tartaric acid and citric acid. Of these, α-hydroxycarboxylic acids are preferred and glycolic acid, lactic acid and malic acid are more preferred. Organic acids include phosphoric acid, sulfuric acid, nitric acid and hydrochloric acid, of which phosphoric acid is preferred.

As Component (B), two or more of the above-described cationic surfactants and tertiary amine type compounds or salts thereof may be used in combination. Its (their) content in the hair cosmetic composition of the present invention is preferably from 0.1 to 20 wt. %, more preferably from 0.1 to 10 wt. %, even more preferably from 0.5 to 5 wt. %, still more preferably from 1 to 4 wt. % in view of improving the feeling to the touch during from application to rinsing and stability of the system.

Examples of the silicone as Component (C) include dimethylpolysiloxane, polyether-modified silicones, amino-modified silicones, carboxy-modified silicones, methylphenylpolysiloxane, fatty acid-modified silicones, aliphatic alcohol-modified silicones, epoxy-modified silicones, fluorine-modified silicones, cyclic silicones, and alkyl-modified silicones. Of these, dimethylpolysiloxanes, polyether-modified silicones, and amino-modified silicones are preferred. Use of a dimethylpolysiloxane, a polyether-modified silicone and an amino-modified silicone can impart hair with good lubricity, smoothness and moist feeling, respectively. As the dimethylpolysiloxanes, those having a viscosity of from 5 $mm^2/s$ to 10 million $mm^2/s$ can be used depending on the intended feeling to the touch, wherein those having a viscosity of 10 million $mm^2/s$ are often supplied in the form of an emulsion. Of these, those having a viscosity falling within a range of from 5000 $mm^2/s$ to 10 million $mm^2/s$ are preferred, and those having a viscosity of from 50000 $mm^2/s$ to 10 million $mm^2/s$ are more preferred. The term "polyether-modified silicones" is a generic name of polyoxyethylene-methylpolysiloxane copolymers and poly(oxyethylene-oxypropylene)methylpolysiloxane copolymers and those having various HLBs are known. Examples of the commercially available products thereof include "Silicone KF351A", "Silicone KF353A", "Silicone KF6008", "Silicone KF6016", "Silicone KF6011", and "Silicone KF6012" (each, trade name; product of Shin-etsu Chemical Co., Ltd.), "DC8500" (trade name; product of Dow Corning Corporation), and "SH3771C, "SH3773C", and "SH3775C" (each, trade name; product of Dow Corning Toray Silicone Co., Ltd.). The polyether-modified silicones may preferably have an HLB of from 4 to 18, more preferably from 7 to 11, as measured by the Griffin method. As the amino-modified silicones, amodimethicone oil or an emulsion thereof is usable. Their commercially available products include amodimethicone emulsion "SM8704C" (trade name; product of Dow Corning Toray Silicone Co., Ltd.) and "XF-42B1989" (trade name; product of GE Toshiba Silicones).

As Component (C), two or more of the above-described silicones may be used in combination, and its (or their) content in the hair cosmetic composition of the present invention is preferably from 0.005 to 10 wt. %, more preferably from 0.01 to 5 wt. %, even more preferably from 1 to 3 wt. %, by weight of the composition.

The silicones as Component (C) are each dispersed in the hair cosmetic composition, and their average particle size is preferably from 0.001 to 200 μm. From the viewpoint of the stability of the composition, the average particle size is preferably from 0.001 to 10 μm, more preferably from 0.1 to 5 μm. From the viewpoint of improving the feeling to the touch during hair drying, the average particle size is preferably from 50 to 150 μm, more preferably from 80 to 120 μm.

For the purpose of stabilization of the hair cosmetic composition, improvement in the feeling upon use, viscosity regulation, and solubilization and dispersion-emulsification of various bases, a surfactant other than Component (B), that is, an amphoteric or nonionic surfactant may be incorporated in the hair cosmetic composition of the present invention.

As the amphoteric surfactant, carbobetaines having a $C_{8-24}$ alkyl, alkenyl or acyl group, amidobetaines, sulfobetaines, hydroxysulfobetaines, amidosulfobetaines, phosphobetaines and imidazolinium are usable. Counterions of the anionic group of these amphoteric surfactants include hydrogen ions, alkali metal ions, alkaline earth metal ions, ammonium ions and alkanolamine ions, while counterions of the cationic group include halide ions, methosulfate ions, and saccharinate ions.

Preferred amphoteric surfactants include laurylamidopropyl betaine ("AMPHITOL 20AB", trade name; product of Kao Corp.), cocoylamidopropyl betaine ("AMPHITOL 55AB", trade name; product of Kao Corp.), lauryldimethylaminoacetic acid betaine ("AMPHITOL 20BS", trade name; product of Kao Corp.), laurylhydroxysulfobetaine ("AMPHITOL 20H", trade name; product of Kao Corp.), and 2-alkyl-N-carboxymethyl-N-hydroxyethylimidazolinium betaines such as sodium cocoamphoacetate ("AMPHITOL 20YN", trade name; product of Kao Corp.), sodium cocoamphopropionate ("AMPHITOL 20X, Y-B", trade name; product of Kao Corp.) and sodium N-cocoyl acyl-N-carboxyethyl-N-hydroxyethyl ethylenediamine ("Softazoline NS", trade name; product of Kao Corp)

Examples of the nonionic surfactant include polyoxyalkylene alkyl (or alkenyl)ethers added with 1 to 20 moles of EO, PO or butylene oxides (which will hereinafter be abbreviated as "BO") and having an alkyl or alkenyl group with 10 to 20 carbon atoms on average, polyoxyalkylene alkyl phenyl ethers added with 1 to 20 moles of EO or PO and having an alkyl group with 6 to 12 carbon atoms on average, polyoxyalkylene alkyl (or alkenyl)ethers added with 1 to 30 moles, in total, of EO and PO or EO and BO (an EO/PO or EO/BO ratio is in the range of from 0.1/9.9 to 9.9/0.1) and having an alkyl or alklenyl group with 10 to 20 carbon atoms on average, higher fatty acid alkanolamides represented by the following formula (5):

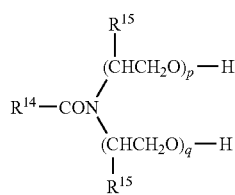

wherein, $R^{14}$ represents a $C_{7-21}$ alkyl or alkenyl group, $R^{15}$ represents a hydrogen atom or a methyl group, p stands for an integer of from 1 to 3 and q stands for an integer of from 0 to 3, or alkylene oxide adducts thereof, sucrose fatty acid esters composed of a fatty acid of 10 to 20 carbon atoms on average and sucrose, and glycerin fatty acid monoesters composed of a fatty acid of 10 to 20 carbon atoms on average and glycerin.

Two or more of these surfactants may be used in combination. Its (or their) content in the whole composition is preferably from 0.1 to 20 wt. %. For obtaining a greater effect, 0.5 to 15 wt. % is more preferred, with 1 to 10 wt. % being even more preferred.

To the hair cosmetic composition of the present invention, proteins ordinarily employed as a hair protecting component can be added in order to further enhance effects of preventing split ends and broken hair.

The term "proteins" embraces proteins, protein hydrolysates and derivatives thereof and they can be extracted or derived from animals or plants. Proteins derived from animals include keratin, elastin, collagen, lactoferrin, casein, α(β)-lactalbumin, globulins, egg albumin and hydrolysates thereof. Of these, keratin, elastin, collagen and casein, and hydrolysates thereof are preferred. Examples of the protein derived from plants include extracts from wheat, malt, oat, barley, corn, rice, soybean, broad bean, silk, seeds of lupine, potatoes, and apricot kernel, and hydrolysates thereof. Of these, proteins from wheat, soybean and silk, and hydrolysates thereof are preferred. As the protein, two or more of the above-described ones may be used in combination, and its (or their) content in the whole composition is preferably 0.01 to 5 wt. %, more preferably from 0.05 to 4 wt. %, even more preferably from 0.1 to 3 wt. %.

To the hair cosmetic composition of the present invention, a cationic polymer conventionally employed as a component for improving the feeling to the touch may be added in order to further improve the feeling upon use.

Examples of the cationic polymer include polydimethyldiallylammonium chlorides, acrylamidopropyltrimethylammonium chloride/acrylate copolymers, acrylamide/dimethyldiallylammonium chloride copolymers, methylvinylimidazolinium chloride/vinylpyrrolidone copolymers, hydroxyethyl cellulose/diallyldimethylammonium chloride copolymers, diethylsulfates of vinylpyrrolidone/dimethylaminoethyl methacrylate copolymers, vinylpyrrolidone/dimethylaminoethylmethyl methacrylate copolymers, vinylpyrrolidone/alkylaminoacrylate/vinylcaprolactam copolymers, vinylpyrrolidone/dimethylaminopropylmethacrylamide copolymers, chlorinated O-[2-hydroxy-3-(trimethylammonio)propyl]hydroxy cellulose, and guar hydroxypropyltrimonium chloride. Of these, chlorinated O-[2-hydroxy-3-(trimethylammonio)propyl]hydroxy cellulose and guar hydroxypropyltrimonium chloride are preferred from the viewpoint of the feeling. Two or more of these cationic polymers may be used in combination. Its (or their) content in the whole composition is, as a solid content, preferably from 0.01 to 20 wt. %, more preferably from 0.05 to 10 wt. %, even more preferably from 0.1 to 5 wt. %.

The hair cosmetic composition of the present invention can contain, in addition to the above-described components, oil components such as cholesterol and derivatives thereof, petrolatum, lanolin derivatives, and fatty acid esters of polyethylene glycol; high molecular emulsifiers such as polycarboxylic acids, crosslinked carboxylic acid/carboxylate copolymers, crosslinked acrylic acid/acrylate copolymers and acrylamide/butanesulfonic acrylamide copolymers; polyhydric alcohols such as glycerin and sorbitol; humectants; chelating agents such as ethylenediaminetetraacetic acid (EDTA); drugs such as vitamin preparations; amino acids and derivatives thereof; fine particles of a polymer such as polyethylene, polystyrene, poly(methyl methacrylate), nylon or silicone, and hydrophobic products thereof; extracts from animals or plants; ultraviolet absorbers, pearling agents; antiseptics; bactericides; anti-inflammatory agents; anti-dandruffs; pH regulators; colorants; and fragrances, according to the intended use.

The hair cosmetic composition of the present invention can be classified into those used in bath rooms such as hair conditioners, hair treatments and hair packs, and styling agents used outside bath rooms such as hair milks, hair creams and hair waxes.

The hair cosmetic composition of the present invention is adjusted to have a pH of from 1 to 4.5 when applied to hair (i.e. when diluted with water to 20 times the weight of the composition at 25° C.) in view of allowing Component (A) (amphipathic amide lipid) to penetrate into hair sufficiently while suppressing stimulation. The pH is more preferably from 2 to 4, with pH from 3 to 3.8 being even more preferred.

The hair cosmetic composition of the present invention can be provided in any form such as liquid, powder, gel and granule as needed. A liquid composition using water or a lower alcohol as a solvent is preferred, with an aqueous solution being more preferred.

EXAMPLES

The following examples further describe and demonstrate embodiments of the present invention. The examples are given solely for the purpose of illustration and are not to be construed as limitations of the present invention. In the below-described Examples and Comparative Examples, the following amphipathic amide lipids were employed.

The pH in the below description is a value of the composition diluted with water to 20 times the weight of the composition when measured at 25° C.

Examples 1 to 3, and Comparative Examples 1 to 3

Hair conditioners as shown in Table 1 were prepared in a conventional manner and evaluated.

(1) Smoothness and Moist Feeling

About 20 g (about 15 cm to 20 cm in length) of the hair of a Japanese female which hair had not yet been subjected to any chemical treatment such as permanent waving or hair dyeing was treated twice with "Lavenus High Bleach" (trade name; product of Kao Corp.) at 40° C. for 20 minutes (at a bath ratio of 1:1). After shampooing, 2 g of the hair condi- Amphipathic amide lipid A

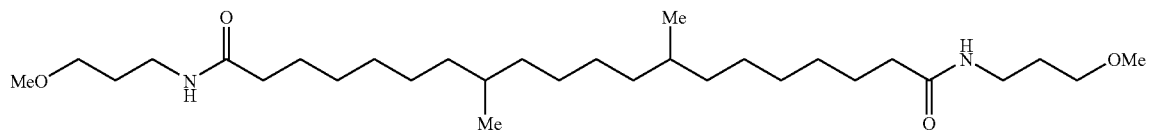

Amphipathic amide lipid B

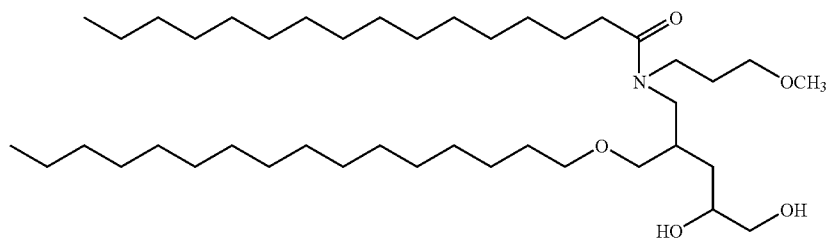

Amphipathic amide lipid C

Ceramide 2

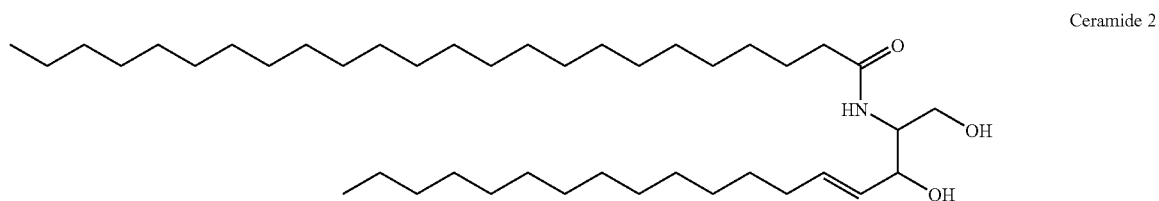

Amphipathic amide lipid D

Ceramide 5

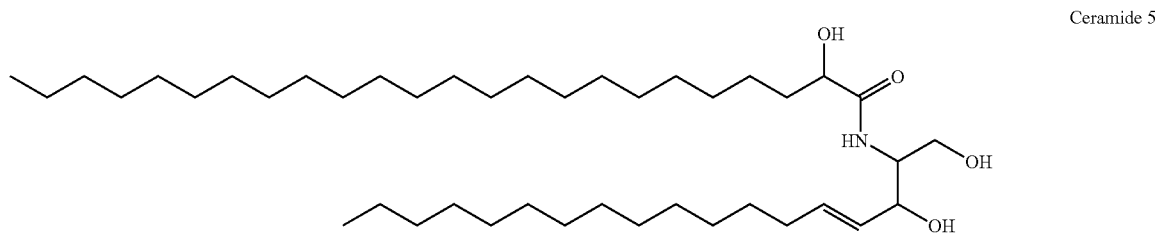

Amphipathic amide lipid E

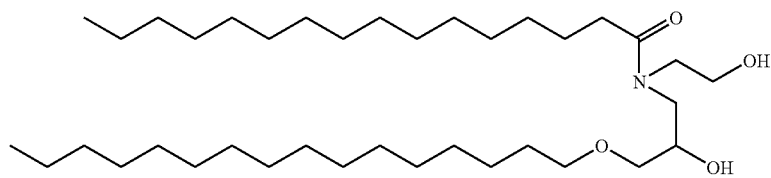

tioner shown in Table 1 was uniformly applied to the hair, rinsed with running water for 30 seconds and then dried with a dryer. The "smoothness" and "moist feeling" of the dried hair was organoleptically evaluated in accordance with the following criteria:

Smoothness:
A: The hair is imparted with natural and sufficient smoothness.
B: The hair is imparted with smoothness.
C: It is difficult to evaluate whether the hair is imparted with smoothness or not.
D: Friction appears among individual hairs.

Moist Feeling:
A: The hair becomes very moist to the touch.
B: The hair becomes moist to the touch.
C: It is difficult to evaluate whether the hair becomes moist to the touch or not.
D: The hair does not become moist to the touch.

(2) Effects of Preventing Split Ends and Breakage of Hair

About 20 g (about 15 to 20 cm long) of the hair of a Japanese female, which had not been subjected to any chemical treatment such as permanent waving and hair dyeing, was treated with "LAVENUS Pure Color Neo Red Nuance" (trade name; product of Kao Corporation) (bath ratio 1:1) at room temperature for 20 minutes. The hair thus treated was then cleansed with a plain shampoo and a plain rinse. The plain shampoo and plain rinse used here have the following compositions, respectively:

| | (wt. %) |
|---|---|
| Plain Shampoo | |
| A 25 wt. % solution of sodium polyoxyethylene(2.5) lauryl ether sulfate | 62.00 |
| Lauric acid diethanolamide | 2.28 |
| Disodium edetate | 0.10 |
| Sodium benzoate | 0.50 |
| Oxybenzone | 0.03 |
| Phosphoric acid (75 wt. %) | 0.10 |
| Dibutylhydroxytoluene | 0.01 |

| | (wt. %) |
|---|---|
| Sodium chloride | 0.80 |
| Red No. 106 | 0.00012 |
| Fragrance | 0.26 |
| Purified water | Balance |
| Plain Rinse | |
| Stearyltrimethylammonium chloride (28 wt. %) | 2.7 |
| Distearyldimethylammonium chloride | 3.6 |
| Cetanol | 2.0 |
| Propylene glycol | 5.0 |
| Methyl p-hydroxybenzoate | 0.1 |
| Deionized water | Balance |

The hair bundle subjected to the above-described cleansing treatment was shampooed once with the conditioner shown in Table 1 and after drying, was brushed predetermined times (100 times/min×90 minutes) at 25 to 27° C. and at 21 to 25% RH. Generation of split ends after brushing was evaluated in accordance with the below-described criteria in comparison with that before brushing.
A: An increase in split ends or breakage of the hair is not recognized.
B: An increase in split ends or breakage of the hair is scarcely recognized.
C: A slight increase in split ends or breakage of the hair is recognized.
D: An increase in split ends or breakage of the hair is recognized.

(3) Storage Stability

In a clear glass bottle, 100 mL of each sample was filled and an accelerated stability test was performed in an incubator (storage temperature of 50° C.×1 month). After completion of the storage term, the bottle was taken out from the incubator and allowed to stand at room temperature for at least 30 minutes. Then, the appearance of the sample was evaluated in accordance with the below-described criteria:
A: no change
B: a slight change (for example, creaming or slight discoloration)
C: an apparent change (for example, separation or gelation)

TABLE 1

| | | | Examples | | | Comparative Examples | | (wt. %) |
|---|---|---|---|---|---|---|---|---|
| | | | 1 | 2 | 3 | 1 | 2 | 3 |
| (A) | Amphipathic amide lipid A | | 2 | 2 | — | 2 | — | 2 |
| | Amphipathic amide lipid B | | — | — | 2 | — | — | — |
| (B) | Stearyltrimethylammonium chloride | | 3 | 3 | 3 | 3 | 3 | 3 |
| (C) | Dimethylpolysiloxane emulsion*[1] | | 2 | 2 | — | — | 2 | — |
| | Amino-modified silicone emulsion*[2] | | — | 0.5 | 0.5 | — | — | 0.05 |
| Others | Behenyl alcohol | | 8 | 8 | 8 | 8 | 8 | 8 |
| | Dipropylene glycol | | 0.5 | 0.5 | 0.5 | 0.5 | 0.5 | 0.5 |
| | Benzyloxy ethanol | | 0.3 | 0.3 | 0.3 | 0.3 | 0.3 | 0.3 |
| | Phenoxy ethanol | | 0.5 | 0.5 | 0.5 | 0.5 | 0.5 | 0.5 |
| | PH regulator (sodium hydroxide, citric acid) | | q.s.*[3] | q.s.*[3] | q.s.*[3] | q.s.*[3] | q.s.*[3] | q.s.*[3] |
| | Purified water | | Balance | Balance | Balance | Balance | Balance | Balance |
| | pH | | 3.5 | 3.5 | 3.5 | 3.5 | 3.5 | 7 |
| Evaluation | Smoothness of hair | | A | A | A | C | C | B |
| | Moist feeling of hair | | A | A | A | B | C | C |
| | Prevention of split ends or breakage of hair | | A | A | B | B | C | C |
| | Storage stability | | B | B | B | B | B | D |

*[1]"CF-2460" (trade name; product of Dow Corning Toray Silicone, a 75 wt. % emulsion, average particle size: about 100 μm)
*[2]"SM8704C" (trade name; product of Dow Corning Toray Silicone, a 40 wt. % emulsion, average particle size: about 0.5 μm)
*[3]An amount to adjust the pH

Example 4

Hair Conditioner

| | (wt. %) |
|---|---|
| Stearyltrimethylammonium chloride | 3.0 |
| Behenyl alcohol | 8.0 |
| Dipropylene glycol | 5.0 |
| Concentrated glycerin | 5.0 |
| Polypropylene glycol | 2.5 |
| Amphipathic amide lipid A | 0.2 |
| Dimethicone-containing emulsion | 2.0 |
| ("CF-2460", trade name; product of Dow Corning Toray, Silicone, a 75 wt. % emulsion, average particle size: about 100 μm) | |
| Malic acid (50 wt. %) | 1.0 |
| Lactic acid (90 wt. %) | 1.7 |
| Sunflower oil | 0.5 |
| Benzyloxyethanol | 1.0 |
| Dipentaerythritol fatty acid ester | 0.1 |
| Phenoxyethanol | 0.1 |
| Sodium hydroxide | An amount to adjust the pH |
| Deionized water | Balance |

The above-described conditioner (pH 3.1) was excellent in smoothness during rinsing, in smoothness and moist feel after drying and also in stability.

Example 5

Hair Treatment

| | (wt. %) |
|---|---|
| N,N-Dimethyloctadecyloxypropylamine | 6.0 |
| Behenyl alcohol | 15.0 |
| Dipropylene glycol | 5.0 |
| Concentrated glycerin | 5.0 |
| Propylene glycol | 2.5 |
| Amphipathic amide lipid C | 0.05 |
| Amphipathic amide lipid D | 0.1 |
| Dimethicone-containing emulsion | 2.5 |
| ("CF-2460", trade name; product of Dow Corning Toray Silicone, a 75 wt. % emulsion, average particle size: about 100 μm) | |
| Amodimethicone-containing emulsion | 0.2 |
| ("SM8704C", trade name; product of Dow Corning Toray Silicone, a 40 wt. % emulsion, average particle size: about 0.5 μm) | |
| Malic acid (50 wt. %) | 1.0 |
| Lactic acid (90 wt. %) | 2.2 |
| Sunflower oil | 1.5 |
| Benzyloxyethanol | 1.0 |
| Dipentaerythritol fatty acid ester | 0.2 |

-continued

| | (wt. %) |
|---|---|
| Oleic cid | 0.1 |
| Phenoxyethanol | 0.5 |
| Coconut oil fatty acid | 0.1 |
| Sodium hydroxide | An amount to adjust the pH |
| Deionized water | Balance |

The above-described treatment (pH 3.2) was excellent in smoothness and moist feeling after drying and also in stability.

Examples 6 to 8, and Comparative Examples 4 to 6

Hair conditioners shown in Table 2 were prepared in a conventional manner and evaluated.

(1) Smoothness and Moist Feeling

Smoothness and moist feeling of the hair conditioners were evaluated in a manner and under criteria similar to those described in Examples 1 to 3 and Comparative Examples 1 to 3.

(2) A Physical Property-Recovering Ratio of Hair

About 20 g (about 15 to 20 cm in length) of the hair of a Japanese female, which had not been subjected to any chemical treatment such as permanent waving and hair dyeing, was treated eight times with "LAVENUS High Bleach" (trade name; product of Kao Corporation) (bath ratio 1:1) at 40° C. for 20 minutes. After each bleaching, the hair was cleansed 90 times with a plain shampoo and a plain rinse, 720 times in total. As the plain shampoo and plain rinse, those used in Examples 1 to 3 and Comparative Examples 1 to 3 were employed.

Dynamic viscoelasticity (storage elastic modulus E': corresponding to the hardness of hair, unit: [Pa]) of each of a hair bundle without treatment (healthy hair), a hair bundle subjected to the above-described bleaching treatment and a hair bundle treated 30 times with the hair conditioner of Table 2 after each bleaching treatment was measured using a viscoelasticity-measuring apparatus "DMTA V" (trade name; product of Rheometric Scientific FE).

Measuring Conditions

Temperature: 22±1° C., relative humidity: 20±1% RH, frequency: 10 Hz

Criteria for Evaluation

A physical property-recovering ratio of hair R represented by the following equation:

$$R=(E_1'-E_n')/(E_1'-E_0')\times 100$$

wherein, $E_0'$ represents a storage elastic modulus of the healthy hair, $E_1'$ represents a storage elastic modulus of the bleached hair and $E_n'$ represents a storage elastic modulus of the hair treated 10 times with each sample after bleaching was calculated as an index of how the physical properties of hair damaged by the bleaching treatment were recovered by the treatment with each sample of Table 1 compared with those of the hair before bleaching (untreated hair):

A: not less than 70 and up to 100

B: not less than 50 but less than 70

C: less than 50

(3) Storage Stability

Storage stability was evaluated in a manner and under criteria similar to those described in Examples 1 to 3 and Comparative Examples 1 to 3.

TABLE 2

| | | \multicolumn{3}{c}{Examples} | \multicolumn{3}{c}{Comparative Examples} (wt. %) |
|---|---|---|---|---|---|---|---|
| | | 6 | 7 | 8 | 4 | 5 | 6 |
| (A) | Amphipathic amide lipid A | 2 | 2 | — | 2 | 2 | — |
| | Amphipathic amide lipid B | — | — | 2 | — | — | — |
| (B) | N,N-dimethyloctadecyloxypropylamine | 4 | — | 4 | — | 4 | 4 |
| | Stearoamidopropyldimethylamine | — | 4 | — | — | — | — |
| | Lactic acid | 2 | — | — | 2 | 2 | 2 |
| | Malic acid | — | 2 | 2 | — | — | — |
| (B') | Stearyltrimethylammonium chloride | — | — | — | 5 | — | — |
| Others | Stearyl alcohol | 11 | 11 | 11 | — | 11 | 11 |
| | Behenyl alcohol | — | — | — | 8 | — | — |
| | DPG | 0.5 | 0.5 | 0.5 | 0.5 | 0.5 | 0.5 |
| | Dimethicone | 1 | 1 | 1 | 1 | 1 | 1 |
| | Benzyloxyethanol | 0.3 | 0.3 | 0.3 | 0.3 | 0.3 | 0.3 |
| | Phenoxyethanol | 0.5 | 0.5 | 0.5 | 0.5 | 0.5 | 0.5 |
| | PH regulator (sodium hydroxide, citric acid) | q.s.* | q.s.* | q.s.* | q.s.* | q.s.* | q.s.* |
| | Purified water | Balance | Balance | Balance | Balance | Balance | Balance |
| | pH | 3.2 | 3 | 3.5 | 3.5 | 7 | 5.5 |
| Evaluation | Smoothness of hair | A | A | A | C | C | C |
| | Moist feeling of hair | A | A | A | C | C | C |
| | Physical property-recovering ratio of hair | A | A | B | C | C | C |
| | Storage stability | B | B | B | B | D | B |

*An amount to adjust the pH

Example 9

Hair Conditioner

| | (wt. %) |
|---|---|
| N,N-dimethyloctadecyloxypropylamine | 2.2 |
| Stearyl alcohol | 6.0 |
| Dipropylene glycol | 5.0 |
| Concentrated glycerin | 5.0 |
| Polypropylene glycol | 2.5 |
| Amphipathic amide lipid A | 0.2 |
| Malic acid (50 wt. %) | 1.0 |
| Lactic acid (90 wt. %) | 1.7 |
| Sunflower oil | 0.5 |
| Benzyloxyethanol | 1.0 |
| Dipentaerythritol fatty acid ester | 0.1 |
| Phenoxyethanol | 0.1 |
| Sodium hydroxide | An amount to adjust the pH |
| Deionized water | Balance |

The above-described conditioner (pH 3.1) was excellent in smoothness during rinsing, in smoothness and moist feeling after drying and also in stability.

Example 10

Hair Treatment

| | (wt. %) |
|---|---|
| N,N-Dimethyloctadecyloxypropylamine | 4.0 |
| Stearyl alcohol | 11.0 |
| Dipropylene glycol | 5.0 |
| Concentrated glycerin | 5.0 |
| Polypropylene glycol | 2.5 |
| Amphipathic amide lipid C | 0.05 |
| Amphipathic amide lipid D | 0.1 |

-continued

| | (wt. %) |
|---|---|
| Malic acid (50 wt. %) | 1.0 |
| Lactic acid (90 wt. %) | 2.2 |
| Sunflower oil | 1.5 |
| Benzyloxyethanol | 1.0 |
| Dipentaerythritol fatty acid ester | 0.2 |
| Oleic acid | 0.1 |
| Phenoxyethanol | 0.1 |
| Coconut oil fatty acid | 0.1 |
| Sodium hydroxide | An amount to adjust the pH |
| Deionized water | Balance |

The above-described treatment (pH 3.2) was excellent in smoothness and moist feeling after drying and also in stability.

Example 11

Hair Treatment

| | (wt. %) |
|---|---|
| Stearamidopropyldimethylamine | 3.4 |
| Stearyl alcohol | 9.0 |
| Glutamic acid | 1.5 |
| Benzyloxyethanol | 1.5 |
| Dipropylene glycol | 2.5 |
| Phenoxyethanol | 0.1 |
| Amphipathic amide lipid C | 0.1 |
| Amphipathic amide lipid D | 0.1 |
| Malic acid (50 wt. %) | 0.02 |
| Dipentaerythritol fatty acid ester | 0.2 |
| Methylpolysiloxane mixed solution | 2.5 |
| Mixture of highly polymerized methylpolysiloxane and Decamethylcyclopentasiloxane | 2.5 |

-continued

| | (wt. %) |
|---|---|
| Aminoethylaminopropylsiloxane/dimethylsiloxane copolymer emulsion | 2.5 |
| Hydroxyethyl cellulose | 0.3 |
| Paraffin | 0.5 |
| Sodium hydroxide | An amount to adjust the pH |
| Fragrance | 0.5 |
| Purified water | Balance |

The above-described treatment (pH 3.3) was excellent in smoothness during rinsing, in smoothness and moist feeling after drying and also in stability.

Example 12

Hair Conditioner

| | (wt. %) |
|---|---|
| Stearamidopropyldimethylamine | 1.5 |
| Stearyl alcohol | 2.5 |
| Cetyl alcohol | 3.4 |
| Glycolic acid (71 wt. %) | 1.5 |
| Benzyl alcohol | 0.5 |
| Dipropylene glycol | 2.5 |
| Amphipathic amide lipid C | 0.1 |
| Amphipathic amide lipid D | 0.1 |
| Lactic acid (90 wt. %) | 2.4 |
| Metehylpolysiloxane mixed solution | 2.0 |
| Mixture of cyclopentasiloxane and dimethiconol ("DC1501", trade name; product of Dow Corning) | 3.0 |
| Hydroxyethyl cellulose | 0.3 |
| Sodium hydroxide | An amount to adjust the pH |
| Fragrance | 0.4 |
| Purified water | Balance |

The above-described conditioner (pH 3.3) was excellent in smoothness during rinsing, in smoothness and moist feeling after drying and also in stability.

Example 13

Hair Treatment

| | (wt. %) |
|---|---|
| N,N-Dimethyloctadecyloxypropylamine | 3.4 |
| Stearyl alcohol | 9.0 |
| Phosphoric acid (85%) | 1.5 |
| Benzyloxyethanol | 1.5 |
| Dipropylene glycol | 2.5 |
| Phenoxyethanol | 0.1 |
| Amphipathic amide lipid E | 0.1 |
| Malic acid (50 wt. %) | 0.02 |
| Dipentaerythritol fatty acid ester | 0.2 |
| Methylpolysiloxane mixed solution | 2.5 |
| Mixture of highly polymerized methylpolysiloxane and Decamethylcyclopentasiloxane | 2.5 |
| Aminoethylaminopropylsiloxane/dimethylsiloxane copolymer emulsion | 2.5 |
| Hydroxyethyl cellulose | 0.3 |
| Paraffin | 0.5 |
| Sodium hydroxide | An amount to adjust the pH |
| Fragrance | 0.5 |
| Purified water | Balance |

The above-described treatment (pH 3.3) was excellent in smoothness during rinsing, in smoothness and moist feeling after drying and also in stability.

What is claimed is:

1. A hair cosmetic composition comprising the following components (A) to (C):

(A): from 0.2 to 3 wt. % of an amphipathic amide lipid selected from the group consisting of Amphipathic amide lipid A and Amphipathic amide lipid B, which have the following formulae, respectively,

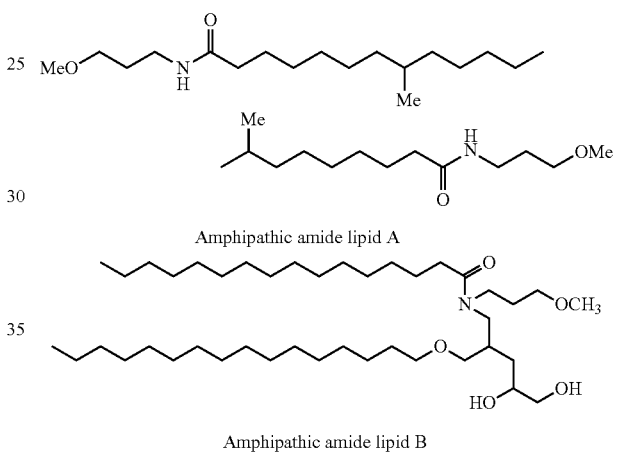

Amphipathic amide lipid A

Amphipathic amide lipid B (B): from 1 to 4 wt. % of a tertiary amine compound selected from the group consisting of N,N-dimethyloctadecyloxypropylamine, stearamidopropyldimethylamine, and mixtures thereof, and (C): from 1 to 3 wt. % of a dimethylpolysiloxane; wherein the composition has a pH of from 1 to 4.5 at 25° C. when diluted with water to 20 times the weight of the composition.

2. The hair cosmetic composition of claim 1 further comprising a surfactant selected from the group consisting of an amphoteric surfactant, nonionic surfactant, and mixtures thereof.

3. The hair cosmetic composition of claim 1, wherein the silicone has an average particle size of from 0.001 to 200 μm.

4. The hair cosmetic composition of claim 1, wherein the silicone has an average particle size of from 0.1 to 5 μm.

5. The hair cosmetic composition of claim 1, wherein the silicone has an average particle size of from 80 to 120 μm.

6. The hair cosmetic composition of claim 1, wherein said pH is from 2 to 4.

7. The hair cosmetic composition of claim 1, wherein said pH is from 3 to 3.8.

* * * * *